(12) United States Patent
Gerardi et al.

(10) Patent No.: US 10,076,858 B2
(45) Date of Patent: Sep. 18, 2018

(54) APPARATUS AND METHOD OF MANUFACTURE OF INTRAOCULAR LENSES

(71) Applicant: NOVARTIS AG, Basel (CH)

(72) Inventors: Lauren Gerardi, Des Plaines, IL (US); Kevin M. Lewellen, Arlington, TX (US)

(73) Assignee: Novartis AG, Basel (CH)

( * ) Notice: Subject to any disclaimer, the term of this patent is extended or adjusted under 35 U.S.C. 154(b) by 269 days.

(21) Appl. No.: 14/961,055

(22) Filed: Dec. 7, 2015

(65) Prior Publication Data

US 2016/0263781 A1    Sep. 15, 2016

Related U.S. Application Data

(60) Provisional application No. 62/131,332, filed on Mar. 11, 2015.

(51) Int. Cl.

| | |
|---|---|
| *B29D 11/00* | (2006.01) |
| *B29C 39/00* | (2006.01) |
| *B29D 11/02* | (2006.01) |
| *B29C 39/36* | (2006.01) |
| *A61F 2/16* | (2006.01) |
| *B29K 83/00* | (2006.01) |

(Continued)

(52) U.S. Cl.
CPC ............ *B29C 39/003* (2013.01); *A61F 2/16* (2013.01); *B29C 39/36* (2013.01); *B29D 11/0048* (2013.01); *B29D 11/023* (2013.01); *B29D 11/026* (2013.01); *B29K 2083/00* (2013.01); *B29K 2905/00* (2013.01); *B29L 2011/0016* (2013.01); *B29L 2031/7532* (2013.01)

(58) Field of Classification Search
CPC . B29D 11/0048; B29D 11/026; B29D 11/023; B29C 39/003; B29C 39/36
See application file for complete search history.

(56) References Cited

U.S. PATENT DOCUMENTS

| | | | |
|---|---|---|---|
| 7,217,112 B2 * | 5/2007 | Kyburz ............... | B29D 11/023 425/117 |
| 2003/0074060 A1 | 4/2003 | Zadno-Azizi et al. | |

(Continued)

OTHER PUBLICATIONS

PCT/US2015/064272, International Searching Authority, "International Search Report", dated Mar. 10, 2016, 5 pgs.

(Continued)

*Primary Examiner* — Mathieu Vargot

(57) ABSTRACT

An apparatus and method for manufacturing intraocular lenses (IOLs) is disclosed. Two mold components (an outer mold component and an inner mold component) of different composition may be employed. The outer mold may be composed of a metal or other refractory material and may serve as the outer die into which a lens forming material can be introduced. The inner mold component may be composed of a softer or more compliant material and may be deployed within the outer mold component. The IOL may be formed by casting the lens-forming material into a shape defined by the space between the two mold components. In certain embodiments, the present disclosure may reduce or eliminate flash in IOLs, improve alignment of their optical surfaces, and/or reduce or eliminate the need for bonded regions.

13 Claims, 1 Drawing Sheet

(51) Int. Cl.
  *B29L 11/00*     (2006.01)
  *B29L 31/00*     (2006.01)

(56) References Cited

U.S. PATENT DOCUMENTS

2006/0001186 A1   1/2006   Richardson et al.
2006/0069431 A1   3/2006   Graney et al.

OTHER PUBLICATIONS

PCT/US2015/064272, International Searching Authority, "Written Opinion", dated Mar. 10, 2016, 6 pgs.

\* cited by examiner

FIG. 1A  FIG. 1B

APPARATUS AND METHOD OF MANUFACTURE OF INTRAOCULAR LENSES

FIELD

This present disclosure relates generally to the field of intraocular lenses (IOLs) and, more particularly, to the manufacturing of IOLs that have a hollow structure or an open framework with one or more internal voids or chambers.

BACKGROUND

The human eye in its simplest terms functions to provide vision by receiving light through a clear outer portion called the cornea, and focusing the image by way of a crystalline lens onto a retina. The quality of the focused image depends on many factors including the size and shape of the eye, and the transparency and focal power of the cornea and the lens.

When age or disease causes the lens to become less transparent, vision deteriorates because of the diminished amount of light that is transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by zonules. Relaxation of the ciliary muscle applies an axial force that tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus on both near and far objects.

As the lens ages, it becomes harder and is less able to change shape in response to movements of the ciliary muscle. This makes it harder for the lens to focus on near objects, a medical condition known as presbyopia. Presbyopia affects nearly all adults by the age of 45 or 50.

When a cataract or other disease requires the removal of the natural lens and replacement with an artificial IOL, the IOL typically is a monofocal lens that provides a suitable focal power for distance vision but requires the use of a pair of spectacles or contact lenses for near vision. Multifocal IOLs, e.g., relying on diffractive patterns to general multiple foci, have been proposed but to date have not been widely accepted.

Certain accommodative IOLs may comprise a hollow shape or an open framework that allows the lens to change its shape by the flexure of certain lens elements. Such complex-shaped IOLs often have one or more internal voids or chambers (which may be filled with an optical fluid), and these voids or chambers may permit the IOL to be more readily deformed. Such complex shapes, however, may be difficult to manufacture since they are often not amenable to casting or extrusion. Assembly from components is also problematic due to the need for proper alignment of the optics and supporting structures. Bonded joints can also result in weak spots when too little material is used or overflow at the bonding sites if too much joinder material is applied.

Accordingly, a need exists for better methods for manufacturing complex-shaped intraocular lenses and the like, such that the structures can be accurately and reproducibly formed.

SUMMARY

The present disclosure generally relates to an apparatus and method for manufacturing intraocular lenses (IOLs). In certain embodiments, two mold components (an outer mold component and an inner mold component) of different composition may be employed. The outer mold may be composed of a metal or other refractory material and may serve as the outer die into which a lens forming material can be introduced. The inner mold component may be composed of a softer or more compliant material and may be deployed within the outer mold component. The IOL may be formed by casting the lens-forming material into a shape defined by the space between the two mold components. In certain embodiments, the present disclosure may reduce or eliminate flash in IOLs, improve alignment of their optical surfaces, and/or reduce or eliminate the need for bonded regions.

In certain embodiments, an apparatus for manufacturing an intraocular lens includes an outer mold constructed of a first material and having a cavity, an inner mold constructed of a second material, the second material being more compressible than the second material, the inner mold configured to be inserted into the cavity of the outer mold such that a space between the inner mold and the outer mold defines the shape of the intraocular lens, and one or more ports in the outer mold, the one or more ports facilitating introduction of a lens-forming material into the space between the inner mold and the outer mold.

In certain embodiments, a method for manufacturing an intraocular lens includes providing an outer mold constructed of a first material and having a cavity and providing an inner mold constructed of a second material, the second material being more compressible than the second material. The method further includes inserting the inner mold into the cavity of the outer mold such that a space between the inner mold and the outer mold defines the shape of the intraocular lens, introducing a lens-forming material into the space between the inner mold and the outer mold and allowing the lens-forming material to solidify, removing the inner mold from the outer mold, and releasing the solidified lens-forming material from the inner mold.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 1A-C illustrate a molding apparatus for casting an accommodative intraocular lens (IOL), according to certain embodiments of the present disclosure.

DETAILED DESCRIPTION

Figure 1C:
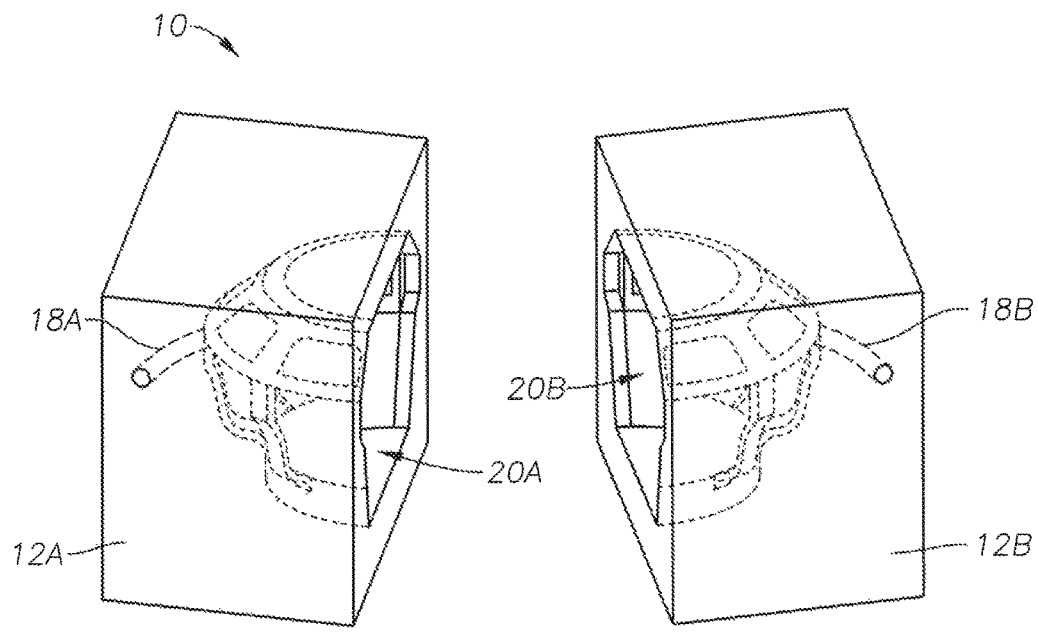

FIGS. 1A-C illustrate a molding apparatus 10 for casting an accommodative intraocular lens (IOL), according to certain embodiments of the present disclosure. In certain embodiments, molding apparatus 10 may include an outer mold 12 and an inner mold 14. In general, an exemplary IOL (e.g., exemplary IOL 50, depicted and described in FIG. 2) may be formed by casting a lens-forming material into a shape defined by a space between the outer mold 12 and the inner mold 14. In certain embodiments, outer mold portion 12 and an inner mold portion 14 may be constructed of materials having differing compressibility, which may provide advantages over other casting techniques (as described in detail below).

Outer mold 12 of molding apparatus 10 may be comprised of a first outer mold portion 12a and a second outer mold portion 12b. In certain embodiments, outer mold 12 may be constructed of a relatively hard, incompressible material. For example, outer mold 12 may be constructed from acetal resin, polycarbonate, polypropylene, steel, aluminum, Teflon, or any other suitable material.

To facilitate casting of an IOL (as described further below), first outer mold portion 12a and a second outer mold portion 12b may each include cavities 20a and 20b, respectively, and these cavities may define an outer shape of an IOL to be casted. Outer mold portions constructed of metal, for example, may be manufactured using 3-D printing, high precision lathing, milling, any combination of these techniques, or any other suitable manufacturing technique. As one specific example, first outer mold portion 12a and a second outer mold portion 12b may each be formed using 3-D printing, and the portions of cavities 20a and 20b corresponding to optical surfaces of a casted IOL may be refined using high precision lathing.

Figure 1C:

Although first component 12a and second component 12b of outer mold 12 are depicted as being divided in a particular location relative to the IOL to be formed, the present disclosure contemplates that first component 12a and second component 12b of outer mold 12 may be divided at any suitable location. As just one example, first component 12a and second component 12b of outer mold 12 may be divided such that dividing line between the two molds does not intersect with the optical surfaces of an IOL formed therein). Additionally, although FIG. 1 illustrates certain features of an IOL as being defined by outer mold 12, the present disclosure contemplates that features of a casted IOL may be defined by any suitable combination of outer mold 12 and inner mold 14. For example, the present disclosure contemplates that cavities 20a and 20b of outer mold 12 may be rotationally symmetric and the complex features of a casted IOL may be defined by the inner mold 14 (e.g., formed in the outer surface of inner mold 14).

Inner mold 14 of molding apparatus 10 may be configured such that, when inserted in the space defined by cavities 20a and 20b of outer mold 12, a space between outer mold 12 and inner mold 14 corresponds to the shape of a desired IOL. For example, inner mold 14 may be inserted in the space defined by cavities 20a and 20b of outer mold 12, and first outer mold portion 12a and a second outer mold portion 12b may be secured together in any suitable manner. Once the portions of outer mold 12 are secured together, a suitable lens-forming material (e.g., silicone) may be introduced into outer mold 12 via ports 18b and 18b (which, despite being depicted at particular location in outer mold 12, may be located at any suitable location). After the lens-forming material has set, the portion of outer mold 12 may be separated, and the inner mold 14 may be removed. The cast IOL and inner mold 14 can subsequently be separated, which may yield a desired hollow or cage-shaped IOL.

In certain embodiments, inner mold 14 may be constructed of a relatively (relative to outer mold 12) soft material, compressible material such as plastic. For example, inner mold 14 may be constructed from polypropylene, teflon, PMMA, acetal resin, hydrophobic acrylic, or any other suitable material.

In certain embodiments, the inner mold 14 may be partially or fully sacrificial in order to release a casted IOL from the mold. For example, inner mold 14 may be formed from a material that can be dissolved with a solvent. As another example, inner mold 14 may be formed from a material that can be fragmented and removed in pieces through one or more openings in the cast IOL. In certain other embodiments, the inner mold 14 may be removed from the cast IOL as a single piece and may remain intact for repeated use. For example, the inner mold 14 may be separated from the cast IOL by cutting and reattaching the IOL at specific locations or by building in unattached joints for subsequent bonding.

In embodiments in which the inner mold is constructed of a material that is more compressible than outer mold 12, the portions of outer mold 12, when secured together prior to casting, may compress and intentionally deform the inner core 14. As a result, a better seal between the portions of outer mold 12 may be achieved (by reducing or eliminating minute gaps between the components of outer mold 12). Consequently, leaking of molding material along the division between portions of outer mold 12 (resulting in a phenomenon known as "flash") may be reduced or eliminated. Because flash must be ground off and the IOL edges polished (which may be a costly, labor intensive finishing step) to achieve the smooth, polished edges necessary to avoid abrading the patient's eye upon implantation, reducing flash in the manner described above may reduce production costs. Moreover, embodiments of the present disclosure may be useful for soft materials that are not easily machined (e.g. hydrogels, silicones or soft acrylics)

Additionally, the above-described casting methods may reduce the number of individual lens components and the bonding of these components, thus simplifying the fabrication process. Furthermore, the above-described casting methods may be useful for fabricating complex-shaped IOL devices or IOLs containing multiple optical components and can be useful to reduce or minimize misalignment of optics.

As one example of an IOL casting process, first outer mold portion 12a and second outer mold portion 12b of outer mold 12 may each be fabricated out of metal using 3D Printing followed by precision lathing/milling of certain surfaces cavities 20a and/or 20b. Similarly, a corresponding inner mold 14 may be fabricated out of a relatively compressible material (e.g., plastic), the inner mold being formed such that, when inserted into the outer mold 12, the space between the inner mold 14 and outer mold 12 corresponds to the structure of a desired IOL. Following fabrication of the outer mold 12 and inner mold 14, the inner mold 14 may be inserted into the outer mold 12, the outer mold portions being secured together so as to compress the inner mold 14 therebetween (e.g., such that at least a portion of outer surface of the inner mold 14 is compressed against a corresponding inner surface of the outer metal 12). Subsequently, and IOL material (e.g., vinyl polysiloxane) can be injected into the space between the inner mold 14 and the outer mold 12 (e.g., via one or more ports 18). After curing of the IOL material, the outer mold 12 can be separated and the inner mold 14 can be removed. The IOL can then be separated from the inner mold 14 (e.g., by cutting selected locations of the IOL, removing inner mold 14, and reattaching the selected portions).

Figure 2:
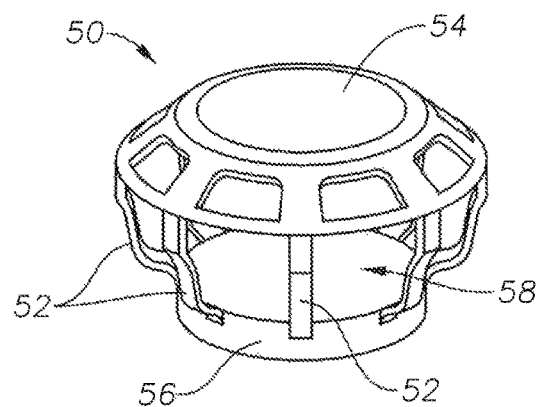
FIG. 2 is a perspective view of an exemplary intraocular lens that can be manufactured using the molding apparatus of FIG. 1.

FIG. 2 is a perspective view of an exemplary IOL 50 that can be manufactured using the molding apparatus of FIG. 1. IOL 50 may include a first optic 54 and a second optic 56 separated by a hollow space 58. First optic 54 may be coupled to second optic 56 via a plurality of struts 52 (which may also be referred to as "haptics"). When inserted into the capsular bag of a patient's eye, the struts 52 may deform in response to axial compression of the capsular bag (resulting ciliary muscle actions), and this deformation may alter the power of the IOL by modifying the first optic 54, modifying the second optic 56, and or modifying the spaced relationship of first optic 54 and second optic 56. For example, axial compression of the capsular bag may cause struts 52 to bend outward, causing the first optic 54 and the second optic 56 to move closer together. Although exemplary IOL is depicted as having a particular structure, the present disclosure contemplates that molding apparatus 10 may be configured to fabricate IOL having a variety of different structures.

In certain embodiments, the lens forming material can be a silicone fluid that is cross-linked in situ during the casting process. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydimethylsiloxanes and methacrylate, and acrylate functional siloxanes. In other embodiments the lens-forming materials can be a hydrogel or a hydrophobic acrylic, such as the AcrySof® acrylic.

The term intraocular lens or "IOL" is used herein to refer to any lens or lens component adapted to be inserted into a patient's eye. Such a lens can be phakic or aphakic (also referred to in the art as pseudophakic) to restore, improve, or partially correct vision. Phakic lenses are used in conjunction with the natural lens of an eye to correct refractive errors such as myopia (near-sightedness), hyperopia (far-sightedness) and astigmatism, coma or other higher order refractive errors (blurred vision due to poor light focusing on the retina due to an irregularly shaped cornea or, in some instances, an irregularly shaped natural lens). An aphakic or pseudophakic lens is inserted in the eye subsequent to removal of the natural lens due to disease, e.g., a cataract or clouding of the natural lens. The aphakic or pseudophakic lens can also restore, improve, or partially correct vision by providing a power comparable to that of the natural lens and can also correct myopia, hyperopia or other refractive errors. Either type of lens may be implanted in the anterior chamber in front of the iris or in the posterior chamber behind the iris and in front of the natural lens or in the region where the natural lens was before removal.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An apparatus for manufacturing an intraocular lens, comprising
   an outer mold constructed of a first material, the outer mold comprising:
      a first outer mold portion; and
      a second outer mold portion, the second outer mold portion being configured to be secured to the first outer mold portion such that the first outer mold portion and the second outer mold portion collectively define a cavity of the outer mold;
   an inner mold constructed of a second material, the second material being more compressible than the first material, the inner mold configured to be inserted into the cavity of the outer mold such that a space between the inner mold and the outer mold defines the shape of the intraocular lens, wherein the inner mold is sized such that, when inserted into the cavity, the outer mold compresses at least a portion of the inner mold;
   one or more ports in the outer mold, the one or more ports facilitating introduction of a lens-forming material into the space between the inner mold and the outer mold.

2. The apparatus of claim 1, wherein the cavity comprises an at least partially patterned inner surface.

3. The apparatus of claim 1, wherein the outer mold comprises an at least partially patterned outer surface.

4. The apparatus of claim 1, wherein:
   the first material comprises a metal material; and
   the second material comprises a plastic material.

5. The apparatus of claim 1, wherein the inner mold is reusable.

6. A method for manufacturing an intraocular lens, comprising
   providing an outer mold constructed of a first material, the outer mold comprising:
      a first outer mold portion; and
      a second outer mold portion, the second outer mold portion being configured to be secured to the first outer mold portion such that the first outer mold portion and the second outer mold portion collectively define a cavity of the outer mold;
   providing an inner mold constructed of a second material, the second material being more compressible than the first material;
   inserting the inner mold into the cavity of the outer mold such that a space between the inner mold and the outer mold defines the shape of the intraocular lens, wherein the inner mold is sized such that, when inserted into the cavity, the outer mold compresses at least a portion of the inner mold;
   introducing a lens-forming material into the space between the inner mold and the outer mold and allowing the lens-forming material to solidify; and
   removing the inner mold from the outer mold; and
   releasing the solidified lens-forming material from the inner mold.

7. The method of claim 6, wherein the lens-forming material comprises a polymeric material.

8. The method of claim 6, wherein the cavity comprises an at least partially patterned inner surface.

9. The method of claim 6, wherein the outer mold comprises an at least partially patterned outer surface.

10. The method of claim 6, wherein the lens-forming material comprises a silicone material.

11. The method of claim 6, wherein releasing the solidified lens-forming material from the inner mold comprises fragmentation of the inner mold.

12. The method of claim 6, wherein releasing the solidified lens-forming material from the inner mold comprises at least partially dissolving the inner mold with a solvent.

13. The method of claim 6, wherein releasing the solidified lens-forming material from the inner mold comprises cutting a selected location on the solidified lens-forming material.

\* \* \* \* \*